(12) United States Patent
Thukral et al.

(10) Patent No.: US 10,757,328 B2
(45) Date of Patent: Aug. 25, 2020

(54) EYE TRACKING USING VIDEO INFORMATION AND ELECTROOCULOGRAPHY INFORMATION

(71) Applicant: Microsoft Technology Licensing, LLC, Redmond, WA (US)

(72) Inventors: Vaibhav Thukral, Kirkland, WA (US); Chris Aholt, Newcastle, WA (US); Christopher Maurice Mei, Redmond, WA (US); Bill Chau, Sammamish, WA (US); Nguyen Bach, Kirkland, WA (US); Lev Cherkashin, Redmond, WA (US); Jaeyoun Kim, Fremont, CA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 177 days.

(21) Appl. No.: 15/390,410

(22) Filed: Dec. 23, 2016

(65) Prior Publication Data

US 2018/0184002 A1 Jun. 28, 2018

(51) Int. Cl.
*A61B 3/00* (2006.01)
*A61B 3/113* (2006.01)
(Continued)

(52) U.S. Cl.
CPC ....... *H04N 5/23241* (2013.01); *A61B 3/0025* (2013.01); *A61B 3/113* (2013.01);
(Continued)

(58) Field of Classification Search
CPC ....... A61B 3/0025; A61B 3/113; A61B 3/145; A61B 5/0496; G06F 1/3203; G06F 3/013;
(Continued)

(56) References Cited

U.S. PATENT DOCUMENTS 8,235,529 B1 * 8/2012 Raffle .................. A61B 3/113
351/209
8,434,868 B2 5/2013 Sato et al.
(Continued)

FOREIGN PATENT DOCUMENTS

EP 2587341 A1 5/2013

OTHER PUBLICATIONS

Du, et al., "Online Vigilance Analysis Combining Video and Electrooculography Features", In Proceedings of International Conference on Neural Information Processing, Nov. 15, 2012, pp. 447-454.
(Continued)

*Primary Examiner* — Christopher S Kelley
*Assistant Examiner* — Asmamaw G Tarko
(74) *Attorney, Agent, or Firm* — Arent Fox LLP (57) ABSTRACT

Disclosed are an apparatus and a method of low-latency, low-power eye tracking. In some embodiments, the eye tracking method operates a first sensor having a first level of power consumption that tracks positions of an eye of a user. In response to detection that the eye does not change position for a time period, the method stops operation of the first sensor and instead operates a second sensor that detects a change of position of the eye. The second sensor has a level of power consumption lower than the level of power consumption of the first sensor. Once the eye position changes, the second sensor resumes operation.

19 Claims, 8 Drawing Sheets (51) Int. Cl.
    A61B 3/14      (2006.01)
    A61B 5/0496    (2006.01)
    G06F 3/01      (2006.01)
    G06K 9/00      (2006.01)
    G06T 7/00      (2017.01)
    G06T 7/246     (2017.01)
    G06T 7/292     (2017.01)
    G06T 7/73      (2017.01)
    H04N 5/232     (2006.01)
    G06F 1/16      (2006.01)
    G06F 1/3234    (2019.01)
    G06F 3/03      (2006.01)
    G06F 1/3203    (2019.01)

(52) U.S. Cl.
    CPC ............ *A61B 3/145* (2013.01); *A61B 5/0496* (2013.01); *G06F 1/163* (2013.01); *G06F 1/1686* (2013.01); *G06F 1/3203* (2013.01); *G06F 1/325* (2013.01); *G06F 3/011* (2013.01); *G06F 3/013* (2013.01); *G06F 3/015* (2013.01); *G06F 3/0304* (2013.01); *G06K 9/00604* (2013.01); *G06T 7/0014* (2013.01); *G06T 7/248* (2017.01); *G06T 7/292* (2017.01); *G06T 7/74* (2017.01); *G06T 2207/30041* (2013.01)

(58) Field of Classification Search
    CPC ...... G06K 9/00604; G06T 2207/30041; G06T 7/0014; G06T 7/248; G06T 7/292; G06T 7/74; H04N 5/23241
    USPC ........................................................ 348/78
    See application file for complete search history.

(56) References Cited

U.S. PATENT DOCUMENTS

| | | |
|---|---|---|
| 2007/0273611 A1 | 11/2007 | Torch |
| 2011/0170065 A1 | 7/2011 | Sugio et al. |
| 2011/0170066 A1 | 7/2011 | Sugio et al. |
| 2011/0178784 A1 | 7/2011 | Sato et al. |
| 2013/0033677 A1 | 2/2013 | MacDougall et al. |
| 2013/0135204 A1 | 5/2013 | Raffle et al. |
| 2014/0081117 A1 | 3/2014 | kato et al. |
| 2014/0226131 A1 | 8/2014 | Lopez et al. |
| 2014/0313129 A1* | 10/2014 | Elvesjo ................. G06F 1/3287 345/156 |
| 2015/0058649 A1* | 2/2015 | Song .................... G06F 1/3231 713/323 |
| 2015/0126845 A1 | 5/2015 | Jin et al. |
| 2015/0309568 A1* | 10/2015 | Miki ...................... G06F 3/013 345/173 |

OTHER PUBLICATIONS

Shawkat, et al., "Eye movement tics", In British Journal of Ophthalmology, vol. 76, Issue 11, Nov. 1, 1992, pp. 697-699.

Vicente, et al., "Eye-tracking capabilities of low-cost EOG system", "In Proceedings of 36th Annual International Conference of the IEEE Engineering in Medicine and Biology Society", Aug. 26, 2014, pp. 610-613.

"International Search Report and Written Opinion Issued in PCT Patent Application No. PCT/US2017/066910", dated Jun. 6, 2018, 14 Pages.

Kornilova, et al., "Vestibular-ocular interaction and weightlessness (microgravity)", Retrieved on: Sep. 13, 2016.

* cited by examiner

EYE TRACKING USING VIDEO INFORMATION AND ELECTROOCULOGRAPHY INFORMATION

BACKGROUND

Eye tracking is a process of tracking the motion of one or both of a person's eyes relative to the person's head. Based on acquired information of the eye positions, eye tracking can be used as one type of input for human-computer interaction. One method of eye tracking is based on video oculography (VOG). VOG is a non-invasive, video based method of measuring eye motion. Light (e.g., infrared light) illuminates an eye and is reflected from the eye. A video camera senses the reflected light and records images of the eye. Based on the images of the eye, the eye tracking system recognizes the pupil and tracks locations of the center of the pupil over time. However, the computing power needed for tracking the pupil in the images usually causes latency. Furthermore, the light source, video camera and processor of the eye tracking system consume a notable amount of power.

SUMMARY

Introduced here are an apparatus and a method (collectively and individually, "the technique introduced here") of low-latency, low-power eye tracking. In some embodiments, the method operates a first sensor that tracks positions of the user eye. In response to detection that the eye does not change position for a time period, the method stops operation of the first sensor and instead operates a second sensor that detects a change of position of the eye. The second sensor has a level of power consumption lower than the level of power consumption of the first sensor. Once the eye position changes, the second sensor resumes operation. The overall power consumption is reduced because the first sensor does not need to run all the time.

In some other embodiments, a method operates a first sensor and a second sensor that track positions of the user eye. The second sensor has a second level of power consumption that is lower than the first level of power consumption of the first sensor. The first sensor also operates at a first frame rate that is lower than the second frame rate at which the second sensor operates. The method determines positions of the eye at keyframes based on signals collected from the first sensor at the first frame rate. The method further determines positions of the eye at regular frames based on signals collected from the second sensor at the second frame rate. Since the first sensor only needs to operate at keyframes, the overall power consumption is reduced.

Other aspects of the disclosed embodiments will be apparent from the accompanying figures and detailed description.

This Summary is provided to introduce a selection of concepts in a simplified form that are further explained below in the Detailed Description. This Summary is not intended to identify key features or essential features of the claimed subject matter, nor is it intended to be used to limit the scope of the claimed subject matter.

BRIEF DESCRIPTION OF THE DRAWINGS

One or more embodiments of the present disclosure are illustrated by way of example and not limitation in the figures of the accompanying drawings, in which like references indicate similar elements.

DETAILED DESCRIPTION

In this description, references to "an embodiment," "one embodiment" or the like mean that the particular feature, function, structure or characteristic being described is included in at least one embodiment introduced here. Occurrences of such phrases in this specification do not necessarily all refer to the same embodiment. On the other hand, the embodiments referred to also are not necessarily mutually exclusive.

The following description generally assumes that a "user" of a display device is a human. Note, however, that a display device according to the disclosed embodiments can potentially be used by a user that is not human, such as a machine or an animal. Hence, the term "user" can refer to any of those possibilities, except as may be otherwise stated or evident from the context. Further, the term "optical receptor" is used here as a general term to refer to a human eye, an animal eye, or a machine-implemented optical sensor designed to detect an image in a manner analogous to a human eye. Thus, the term "eye tracking" is used henceforth in this description as a general term to refer to a process of tracking movement or position of an optical receptor such as a human eye, an animal eye, or a machine-implemented optical sensor.

Head-mounted display (HMD) devices and other near-to-eye display (NED) systems may include components to track motion of the user's eye. A device as disclosed herein can include two different sensors for eye tracking, e.g., a first sensor and a second sensor. The first sensor has a level of power consumption higher than the level of power consumption of the second sensor. Alternatively, the first sensor can have a latency level higher than the latency level of the second sensor. By dynamically switching between the sensors and combining the signals collected by the sensors, the disclosed device can achieve accurate eye tracking with lower power consumption and lower latency than conventional eye tracking systems.

In some embodiments, the first sensor is a camera for conducting video oculography (VOG), and the second sensor is an electrooculography (EOG) sensor for collecting EOG signals. To minimize power consumption, the device operates the camera for a specified amount of time. For the rest of time, the device only uses the EOG signals to predict the point of gaze (i.e., eye direction). The EOG sensor is more power efficient than the VOG camera, and processing of the EOG signals requires fewer computation resources than processing of the VOG data. The device can resume operation of the camera if a calibration of the eye position is needed.

FIGS. 1 through 7 and related text describe certain embodiments of a technology for eye tracking using sensors that have different levels of power consumption. However, the disclosed embodiments are not limited to NED systems or HMD devices and have a variety of possible applications, such as in computer monitor systems, head-up display (HUD) systems, and video game systems. For example, a device can perform a foveated rendering based on the detected eye positions. For foveated rendering, a fixation point (also referred to as gaze point) is determined based on the eye tracking. Then the image portion at the fixation point can be rendered in a resolution that is higher than the resolution for the rest of the image. Alternatively, the rest of the image other than the fixation point can be blurred. All such applications, improvements, or modifications are considered within the scope of the concepts disclosed here.

Figure 1:
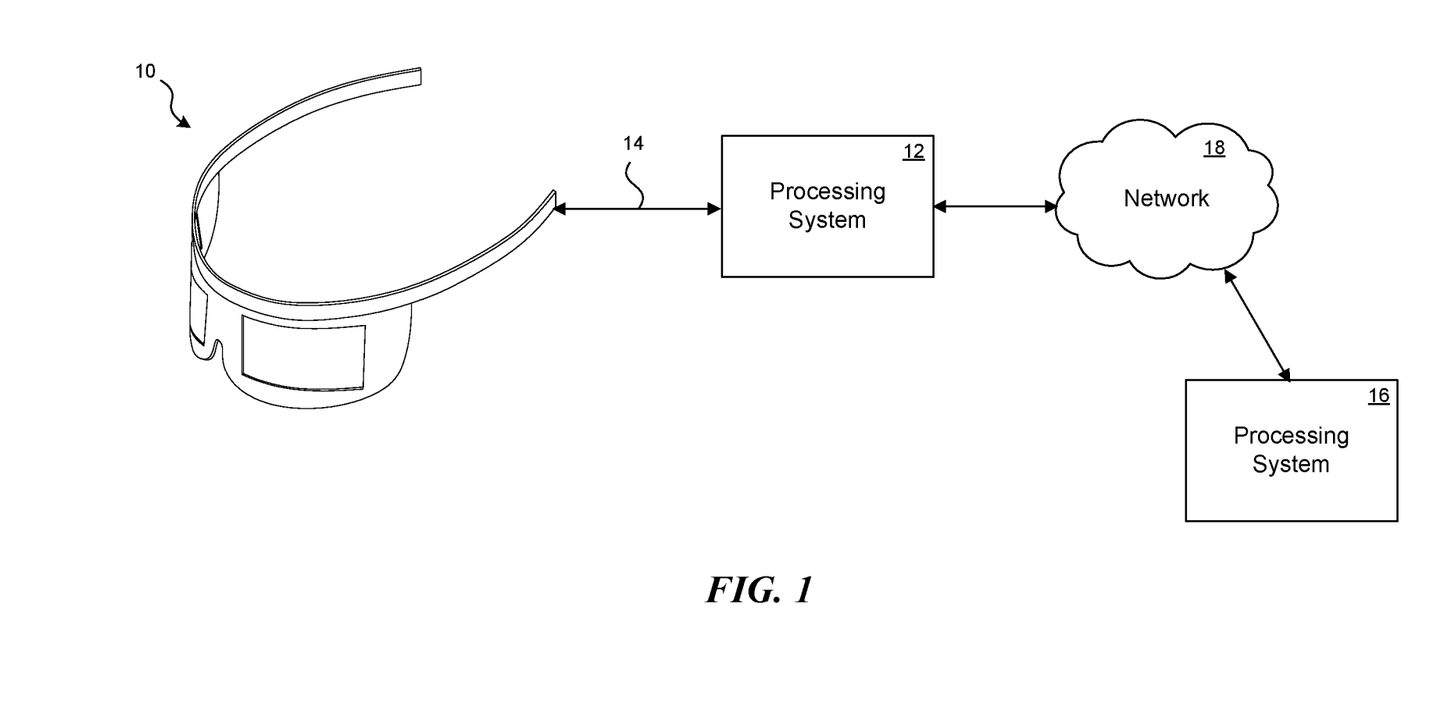
FIG. 1 shows an example of an environment in which a virtual reality (VR) or augmented reality (AR) enabled head-mounted display device (hereinafter "HMD device") can be used.

FIG. 1 schematically shows an example of an environment in which an HMD device can be used. In the illustrated example, the HMD device 10 is configured to communicate data to and from an external processing system 12 through a connection 14, which can be a wired connection, a wireless connection, or a combination thereof. In other use cases, however, the HMD device 10 may operate as a standalone device. The connection 14 can be configured to carry any kind of data, such as image data (e.g., still images and/or full-motion video, including 2D and 3D images), audio, multimedia, voice, and/or any other type(s) of data. The processing system 12 may be, for example, a game console, personal computer, tablet computer, smartphone, or other type of processing device. The connection 14 can be, for example, a universal serial bus (USB) connection, Wi-Fi connection, Bluetooth or Bluetooth Low Energy (BLE) connection, Ethernet connection, cable connection, digital subscriber line (DSL) connection, cellular connection (e.g., 3G, LTE/4G or 5G), or the like, or a combination thereof. Additionally, the processing system 12 may communicate with one or more other processing systems 16 via a network 18, which may be or include, for example, a local area network (LAN), a wide area network (WAN), an intranet, a metropolitan area network (MAN), the global Internet, or combinations thereof.

Figure 2:
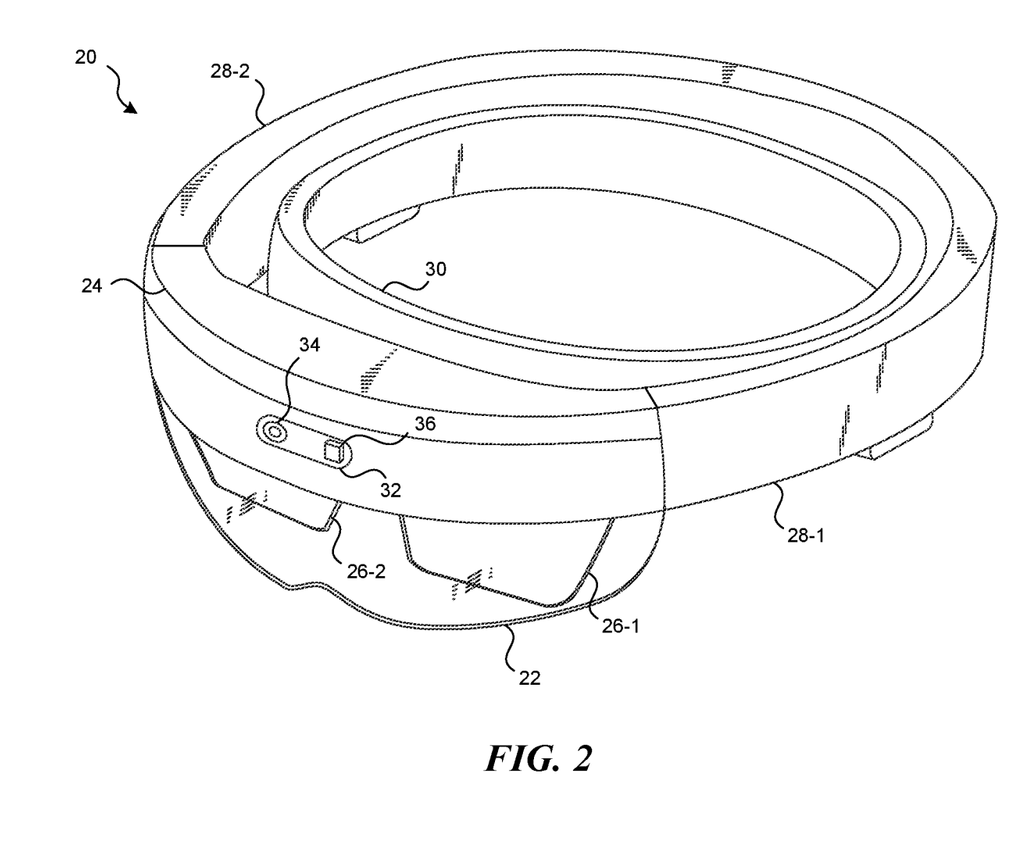
FIG. 2 illustrates a perspective view of an example of an HMD device.

FIG. 2 shows a perspective view of an HMD device 20 that can incorporate the features being introduced here, according to certain embodiments. The HMD device 20 can be an embodiment of the HMD device 10 of FIG. 1. The HMD device 20 has a protective sealed visor assembly 22 (hereafter the "visor assembly 22") that includes a chassis 24. The chassis 24 is the structural component by which display elements, optics, sensors and electronics are coupled to the rest of the HMD device 20. The chassis 24 can be formed of molded plastic, lightweight metal alloy, or polymer, for example.

The visor assembly 22 includes left and right AR displays 26-1 and 26-2, respectively. The AR displays 26-1 and 26-2 are configured to display images overlaid on the user's view of the real-world environment, for example, by projecting light into the user's eyes. Left and right side arms 28-1 and 28-2, respectively, are structures that attach to the chassis 24 at the left and right open ends of the chassis 24, respectively, via flexible or rigid fastening mechanisms (including one or more clamps, hinges, etc.). The HMD device 20 includes an adjustable headband (or other type of head fitting) 30, attached to the side arms 28-1 and 28-2, by which the HMD device 20 can be worn on the user's head.

The chassis 24 may include various fixtures (e.g., screw holes, raised flat surfaces, etc.) to which a sensor assembly 32 and other components can be attached. In some embodiments the sensor assembly 32 is contained within the visor assembly 22 and mounted to an interior surface of the chassis 24 via a lightweight metal frame (not shown). A circuit board (not shown in FIG. 2) bearing electronics components of the HMD 20 (e.g., microprocessor, memory) can also be mounted to the chassis 24 within the visor assembly 22.

The sensor assembly 32 includes a depth camera 34 and an illumination module 36 of a depth imaging system. The illumination module 36 emits light to illuminate a scene. Some of the light reflects off surfaces of objects in the scene, and returns back to the imaging camera 34. In some embodiments such as an active stereo system, the assembly can include two or more cameras. The depth camera 34 captures the reflected light that includes at least a portion of the light from the illumination module 36.

The "light" emitted from the illumination module 36 is electromagnetic radiation suitable for depth sensing and should not directly interfere with the user's view of the real world. As such, the light emitted from the illumination module 36 is typically not part of the human-visible spectrum. Examples of the emitted light include infrared (IR) light to make the illumination unobtrusive. Sources of the light emitted by the illumination module 36 may include LEDs such as super-luminescent LEDs, laser diodes, or any other semiconductor-based light source with sufficient power output.

The depth camera 34 may be or include any image sensor configured to capture light emitted by an illumination module 36. The depth camera 34 may include a lens that gathers reflected light and images the environment onto the image sensor. An optical bandpass filter may be used to pass only the light with the same wavelength as the light emitted by the illumination module 36. For example, in a structured light depth imaging system, each pixel of the depth camera 34 may use triangulation to determine the distance to objects in the scene. Any of various approaches known to persons skilled in the art can be used for determining the corresponding depth calculations.

The HMD device 20 includes electronics circuitry (not shown in FIG. 2) to control the operations of the depth camera 34 and the illumination module 36, and to perform associated data processing functions. The circuitry may include, for example, one or more processors and one or more memories. As a result, the HMD device 20 can provide surface reconstruction to model the user's environment, or be used as a sensor to receive human interaction information. With such a configuration, images generated by the HMD device 20 can be properly overlaid on the user's 3D view of the real world to provide a so-called augmented reality. Note that in other embodiments the aforementioned components may be located in different locations on the HMD device 20. Additionally, some embodiments may omit some of the aforementioned components and/or may include additional components not discussed above nor shown in FIG. 2. In some alternative embodiments, the aforementioned depth imaging system can be included in devices that are not HMD devices. For example, depth imaging systems can be used in motion sensing input devices for computers or game consoles, automotive sensing devices, earth topography detectors, robots, etc.

The HMD device 20 can include various user input mechanisms for interacting with a user interface created based on the depth information. For example, the HMD device 20 can include one or more sensors for tracking the positions of the user's eyes and determining a point of gaze. The HMD device 20 then identifies a point in the virtual environment created by the HMD device 20 that corresponds to the point of gaze. Recognizing that the user is gazing at that point, the HMD device 20 can update the user interface in the virtual environment accordingly. Therefore, the user can interact with the user interface by just gazing at a certain point of the user interface, or by gazing at a certain point in conjunction with some other form of input (e.g., verbal command or hand gesture).

Figure 3:
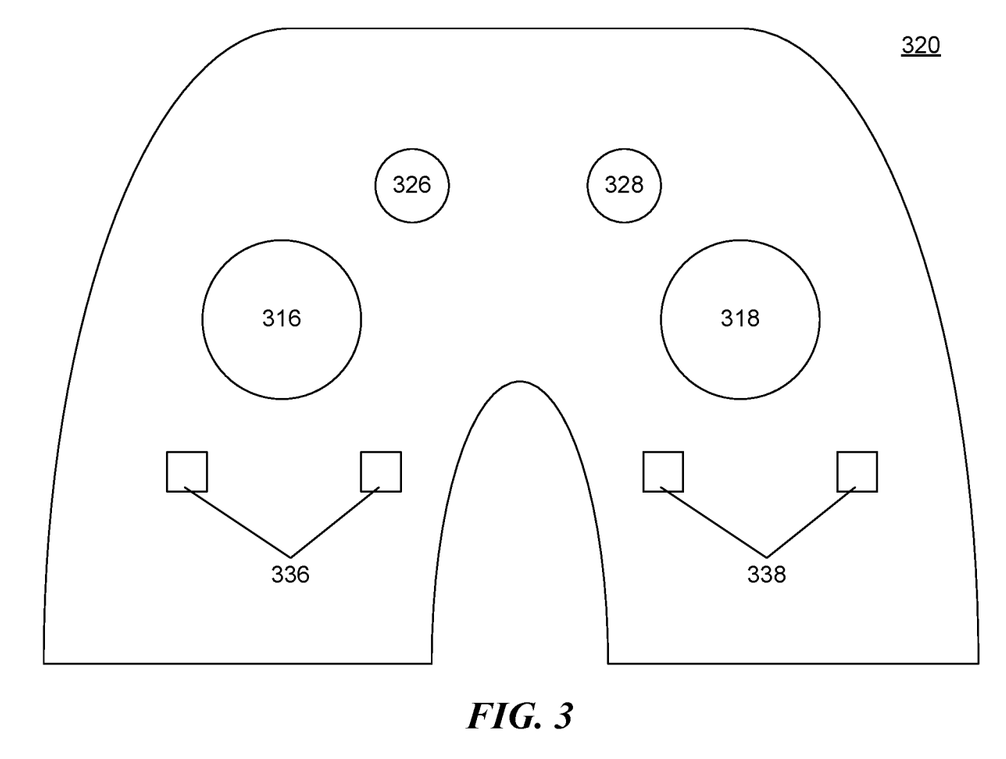
FIG. 3 illustrates an example of an HMD device including different eye tracking sensors.

FIG. 3 shows an example of an HMD device that includes eye-tracking sensors, according to certain embodiments. The HMD device 320 includes cameras 316 and 318 (also referred to as VOG sensors) for capturing video sequences of the user's left and right eyes. In some alternative embodiments, a device can include just one camera for capturing video sequences of one of the eyes. The HMD device 320 can include one or more light sources (e.g., infrared light-emitting diodes) 326 and 328 to provide illumination of the eyes so that the cameras 316 and 318 can capture the video sequences (or images) of the eyes.

The cameras 316 and 318 operate at certain operating cycles (e.g., 30 frames per second). The HMD device 320 can control the operations of the cameras 316 and 318. For example, a processor of the HMD device 320 can send instructions to a control circuit to suspend and resume operation of the cameras 316 and 318. The processor of the HMD device 320 receives and processes the video sequences to identify positions of the pupils. The HMD device 320 can then track and record the movement of the eyes in an X-Y plane. In the X-Y plane, the X-axis coordinate represents the eye movement in the vertical direction (up and down relative to the head); the Y-axis coordinate represents the eye movement in the horizontal direction (left and right relative to the head).

The HMD device 320 further includes two EOG sensors 336 and 338 for eye tracking. Each EOG sensor can include, e.g., two contact points as illustrated in FIG. 3. When a user wears the HMD device 320, the contact points of the EOG sensors 336 and 338 are in contact with the user's skin. In some embodiments, the two contact points of an EOG sensor are placed above and below the eye. In some other embodiments, the two contact points are placed to the left and right of the eye. In yet some other embodiments, each EOG sensor can have more than two contact points.

Through the contacts, the EOG sensors 336 and 338 can measure a corneo-retinal standing potential between the front and the back of the eye. If the eye moves from the center position toward one of the two electrodes, a potential difference occurs between the electrodes. The resulting potential signal is called electrooculogram. Assuming the resting potential (when the eye rests at the middle) remains constant, the recorded potential is a measure of the eye's position.

The VOG sensors 316 and 318 consume more power than the EOG sensor 336 and 338. In addition, because of the computing time needed for processing the video sequences, the VOG sensors 316 and 318 has a higher latency than the EOG sensor 336 and 338 for eye tracking. On the hand, the VOG sensors 316 and 318 have a better accuracy for eye tracking than the EOG sensor 336 and 338.

Trigger-Based Mechanism

To achieve a lower level of power consumption while maintaining accurate eye-tracking, the HMD device 320 can use a combination of the VOG signals and the EOG signals. During eye tracking, the HMD device 320 only turns on the VOG sensors 316 and 318 for a portion of the time period. In some embodiments, the HMD device 320 uses a trigger-based mechanism to control the operation of the VOG sensors 316 and 318. When the eyes do not move, the HMD device 320 turns off the VOG sensors 316 and 318.

EOG sensors 336 and 338 remain operating to monitor the eye movement. Based on the EOG signals, the HMD device 320 can determine in a real time whether the eyes move or not. In other words, the EOG sensors 336 and 338 serve as motion detectors. For example, a processor of the HMD device 320 can calculate a difference between the estimated eye positions based EOG signals between two nearby frames. If the difference of the estimated eye positions is within a specified range (or less than a threshold value), the processor determines that the eye position has not changed yet. Otherwise, the processor detects an eye movement. Once the eyes start to move, the HMD device 320 turns on (triggers) the VOG sensors 316 and 318 to identify the new positions of the eyes. If the eyes stop moving, the HMD device 320 again turns off the VOG sensors 316 and 318. The EOG sensors 336 and 338 continue serving as motion detectors.

Figure 4:
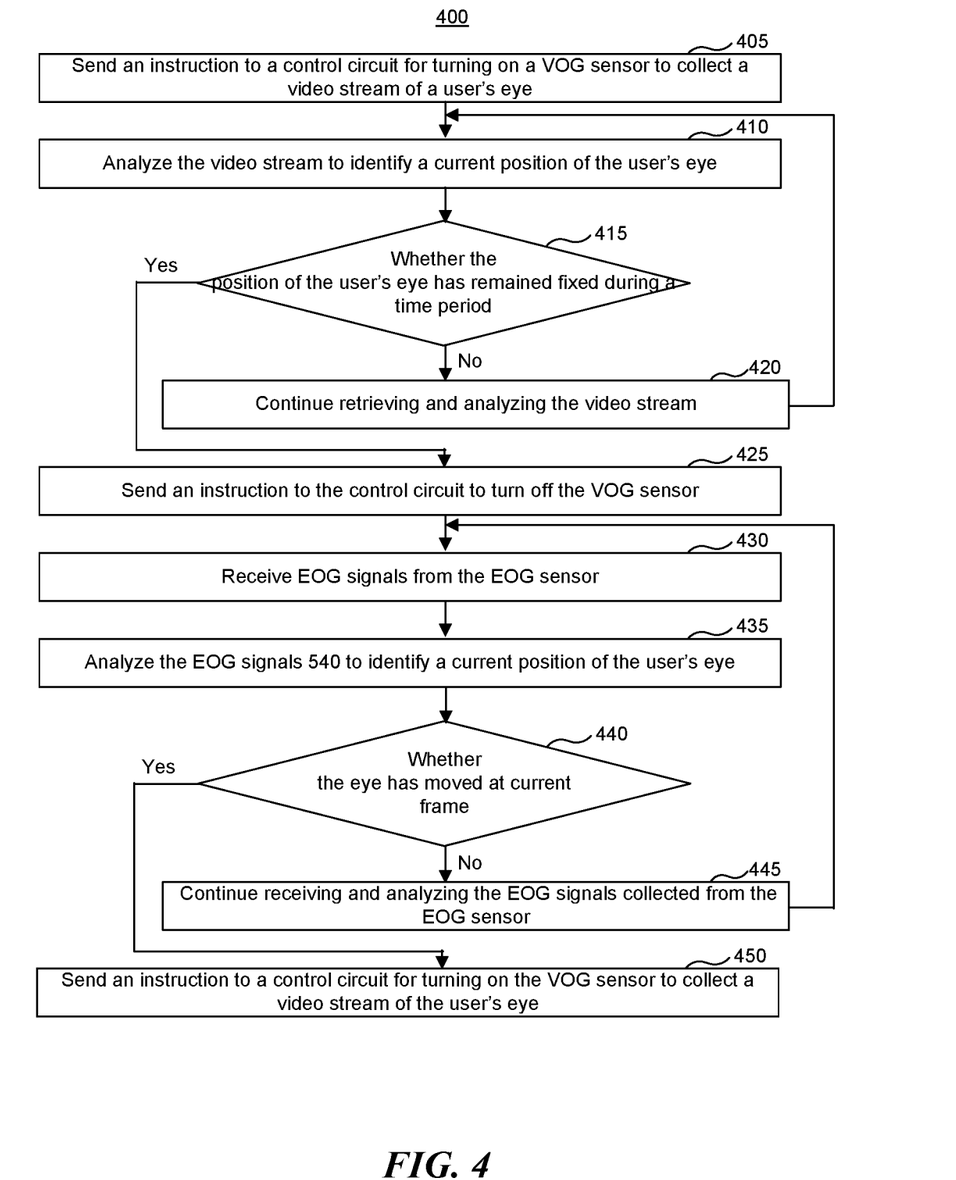
FIG. 4 illustrates a sample process of eye tracking using a trigger-based mechanism.
Figure 5:
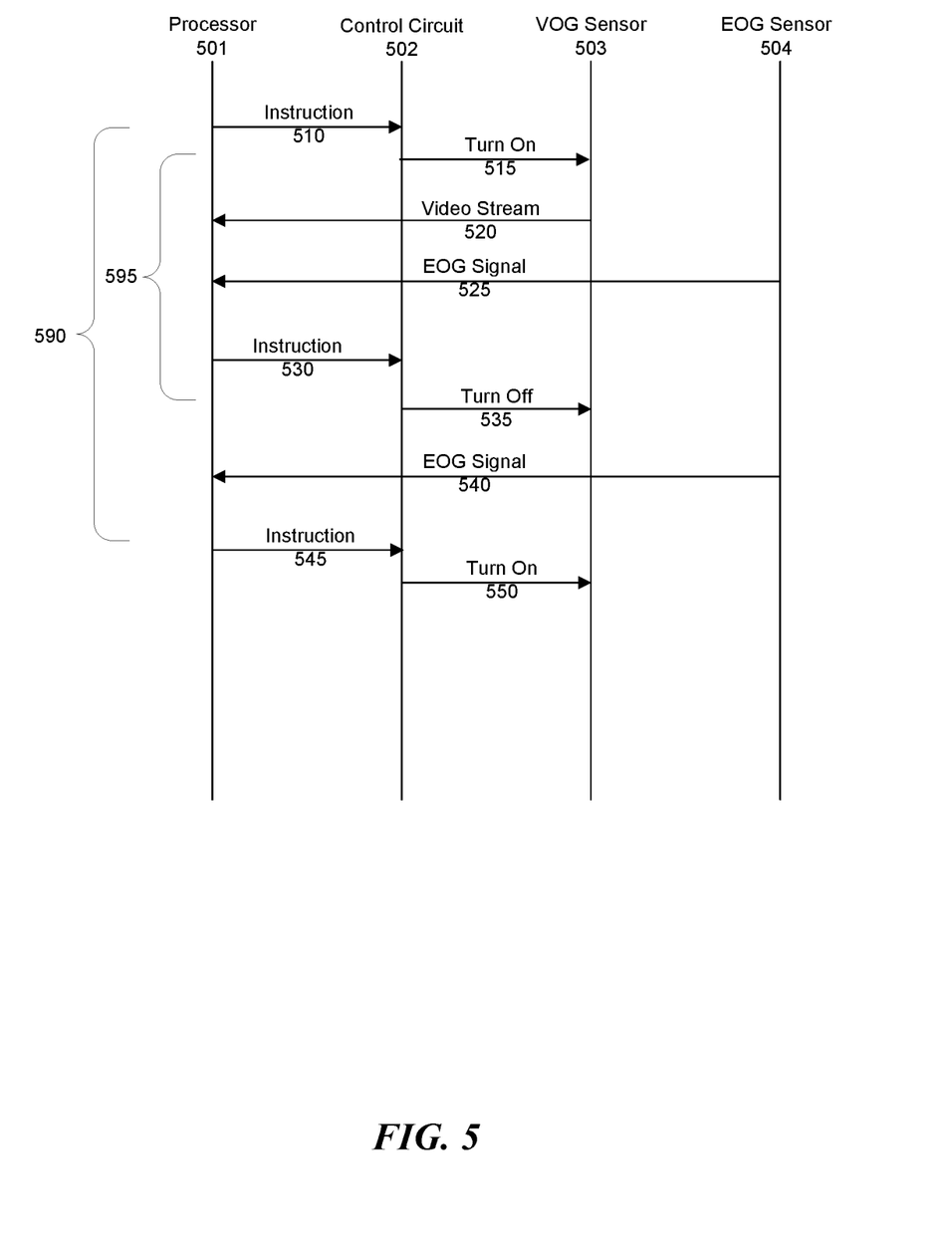
FIG. 5 illustrates information being exchanged between components of an eye tracking device during the process of FIG. 4.

FIG. 4 illustrates a sample process of eye tracking using a trigger-based mechanism, according to certain embodiments. In addition, FIG. 5 illustrates information being exchanged between components of an eye tracking device during the process of FIG. 4, according to certain embodiments. At step 405 of the process 400 as illustrated in FIG. 4, a processor 501 of an eye tracking device (e.g., HMD device 320 as illustrated in FIG. 3) sends an instruction 510 to a control circuit 502 for turning on (515) a VOG sensor 503 to collect a video stream of a user's eye. During a time period when the VOG sensor 530 is on, the eye tracking device operates at a higher level of power consumption than when the VOG sensor 503 is off. The VOG sensor 503 feeds back the video stream 520 to the processor 501 in a real time as the VOG sensor 503 collects the video stream.

In some alternative embodiments, in addition to the video stream 520 from the VOG sensor 503, the processor 501 also continuously receives EOG signals 525 from the EOG sensor 504. The processor can track the eye position based on a combination of the video stream 520 and the EOG signals 525.

At step 410, the processor 501 analyzes the video stream 520 to identify a current position of the user's eye. At step 415, the processor 501 determines whether the position of the user's eye has remained fixed during a time period. In some embodiments, the processor 501 compares the eye positions during that time period. If the differences among the eye positions during that time period are within a specified range (or less than a threshold value), the processor 501 determines that the eye position has remained fixed during that time period. Otherwise, the processor 501 determines that the eye position has moved. In other words, an eye movement has occurred.

If the position of the user's eye has not remained fixed during the time period, at step 420, the processor 501 continues retrieving and analyzing the video stream. If the position of the user's eye has remained fixed during the time period, the eye position likely will continue to remain fixed for some additional time. In that case, there is no need for the VOG sensor 503 to continue operating to track the eye position at a high accuracy, since the EOG sensor 504 with a relatively low accuracy is enough for monitoring the eye movement. At step 425, the processor 501 sends an instruction 530 to the control circuit 502 to turn off (535) the VOG sensor 503. Once the VOG sensor 503 is off, the eye tracking device operates at a lower level of power consumption than when the VOG sensor 503 is on.

At step 430, the processor 501 receives EOG signals 540 from the EOG sensor 504. At step 435, the processor 501 analyzes the EOG signals 540 to identify a current position of the user's eye. The EOG sensor 504 serves as a motion detector for the eye. At step 440, the processor 501 determines whether the eye has moved at the current point in time (current frame). In some embodiments, the processor 501 can calculate a difference between the current eye position and a previous eye position (e.g., an eye position at a frame immediately before the current frame). If the difference between the eye positions is within a specified range (or less than a threshold value), the processor 501 determines that the eye position has not changed.

If the eye has not moved, at step 445, the processor 501 continues receiving and analyzing the EOG signals 540 collected from the EOG sensor 504. If the eye has moved, the device needs a more accurate eye tracking component (e.g., the VOG sensor 503) to accurately identify the eye movement. Thus, at step 450, the processor 501 again sends an instruction 545 to a control circuit 502 for turning on (550) the VOG sensor 503 to collect a video stream of the user's eye. The eye tracking device continues to turn on and off the VOG sensor 503 depending on the eye movement status.

During the time period 590 between the points in time when the processor 501 sends instructions 510 and 545 for turning on the VOG sensor 503, the VOG sensor 503 operates only for a specific amount of time 595. For the rest of time, the device only uses the EOG sensor 504 as a motion sensor for the eye. Compared to A device performing the process 400 consumes less power than a conventional eye tracking device that keeps a VOG sensor turned on throughout the operation. In addition, the processor 501 only analyzes the VOG signals when the VOG sensor 503 is on. Since it takes less computing time to analyze the EOG signals from the EOG sensor 504 than to analyze the video stream from the VOG sensor 503, the process 400 has an advantage of low latency for eye tracking than a conventional process of keeping a VOG sensor turned on throughout the operation.

Keyframe-Based Mechanism

Turning back to FIG. 3, in some embodiments, the HMD device 320 can control the operation of the VOG sensors 316 and 318 using a keyframe-based mechanism. The VOG sensors 316 and 318 operate at a low frame rate (e.g., 5 Hz). In other words, for every 0.2f seconds, the VOG sensors 316 and 318 only need to turn on once to take one picture of each eye. The VOG sensors can remain off for the rest of time. The low frame rate reduces the level of power consumption of the VOG sensors 316 and 318. The points in time when the VOG sensors 316 and 318 operate are referred to as keyframes. In contrast, the low-power sensors, EOG sensors 336 and 338, operate at a higher frame rate (e.g., 200 Hz). In other words, the EOG sensors 336 and 338 collect the EOG signals 200 times for each second. The points in time when the EOG sensors 336 and 338 collect the EOG signals are referred to as regular frames.

The VOG sensors collect the VOG signals at 5 Hz to determine the eye movement at each keyframe (e.g., 5 keyframes per second). For the eye positions between the keyframes, the HMD device uses EOG signals to estimate the eye positions. Because the EOG signals are less accurate than the VOG signals, the estimate eye positions based on EOG signals can be biased. The bias can be removed by using the VOG signals at keyframes as calibration references. For example, a processor can compute the difference between an eye position estimated based on EOG signals and another eye position calculated based on VOG signals at the same keyframe. Note that both VOG sensors and EOG sensors can collect signals at keyframes if the EOG sensors are turned on throughout the operation of the device. Even if there is no EOG signal available at the keyframe, the processor can still compute the difference based on the VOG signals at the keyframe and EOG signals at a regular frame that is close to the keyframe. The difference between the eye positions is treated as the bias. Then the processor can calibrate eye positions estimated based on EOG signals by subtracting the bias from those eye positions.

Figure 6:
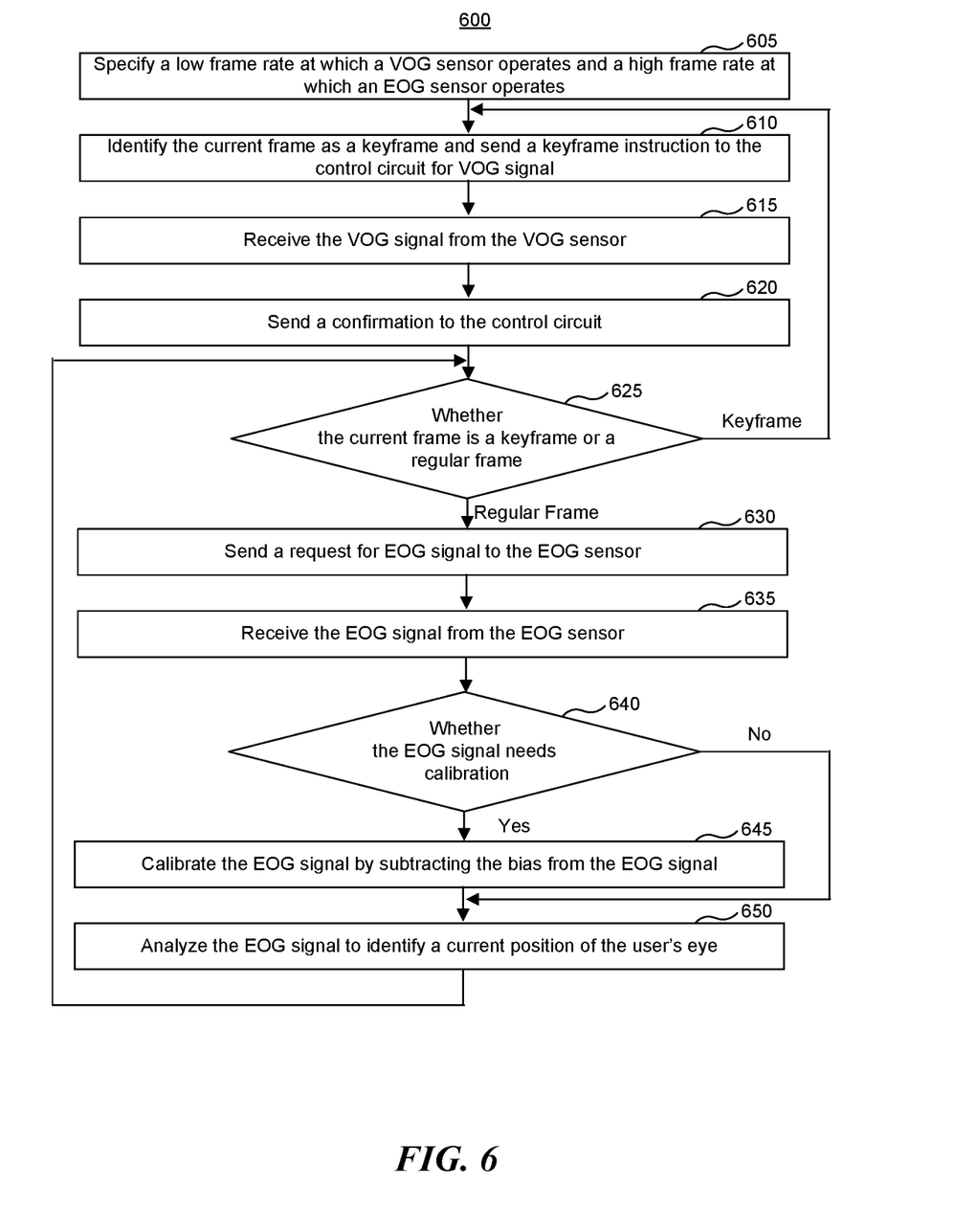
FIG. 6 illustrates a sample process of eye tracking using a keyframe-based mechanism.
Figure 7:
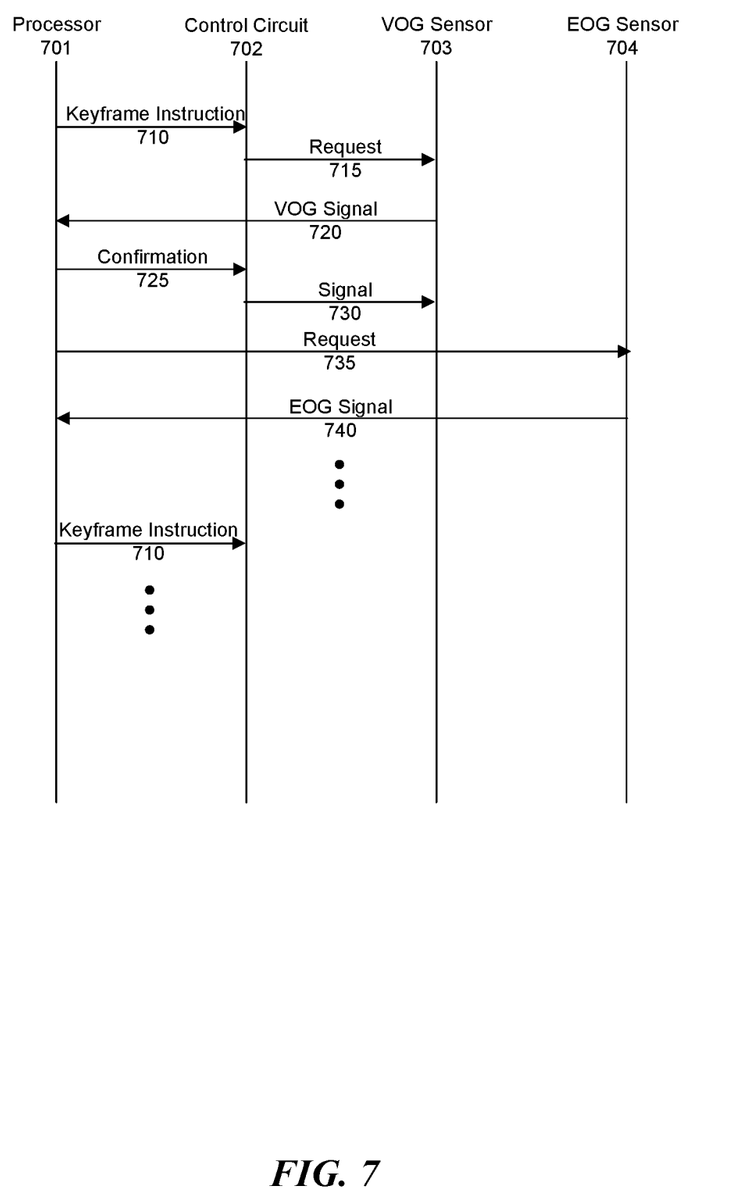
FIG. 7 illustrates information being exchanged between components of an eye tracking device during the process of FIG. 6.

FIG. 6 illustrates a sample process of eye tracking using a keyframe-based mechanism, according to certain embodiments. In addition, FIG. 7 illustrates information being exchanged between components of an eye tracking device during the process of FIG. 6, according to certain embodiments. At step 605 of the process 600 as illustrated in FIG. 6, a processor 701 of an eye tracking device (e.g., HMD device 320 as illustrated in FIG. 3) specifies a low frame rate at which a VOG sensor 703 operates and a high frame rate at which an EOG sensor 704 operates. In some embodiments, the processor 701 specifies the low and high frame rates based on user inputs. In some alternative embodiments, the processor 701 specifies the low and high frame rates based on hardware specifications of the VOG sensor 703 and the EOG sensor 704.

The points in time when the VOG sensor 703 turns on and operates are called keyframes. For example, a VOG sensor operating at a low frame rate of 5 Hz turns on at 5 keyframes per second. The points in time when the EOG sensor 704 turns on and operates are called regular frames. For example, an EOG sensor operating at a high frame rate of 200 Hz turns on at 200 regular frames per second.

At step 610, the processor 701 identifies the current frame as a keyframe and sends a keyframe instruction 710 to the control circuit 702 for VOG signal. Based on the keyframe instruction 710, the control circuit 702 requests (715) the VOG signal from the VOG sensor 703. The VOG sensor 703 recovers from an off stage (or a hibernation stage) and collects the VOG signal.

At step 615, the processor 701 receives the VOG signal 720 from the VOG sensor 703. The VOG signal 720 includes, e.g., an image of a user's eye. At step 620, the processor 701 sends a confirmation 725 to the control circuit 702. Upon receiving the confirmation 725, the control circuit 702 sends a signal 730 to the VOG sensor 703 for turning off the VOG sensor 703. At step 625, the processor 701 analyzes the VOG signal 720 to identify a current position of the user's eye.

In some alternative embodiments, in addition to the VOG signal 720 received from the VOG sensor 703 at the keyframe, the processor 701 also continuously receives EOG signal from the EOG sensor 704 at the keyframe. The processor can track the eye position based on a combination of the VOG signal and the EOG signal.

At step 625, the processor 701 determines whether the current frame is a keyframe or a regular frame. If the current frame is a keyframe, the process 600 proceeds to step 610 to request the VOG signal. If the current frame is a regular frame, at step 630, the processor 701 sends a request (735)

for EOG signal to the EOG sensor 704. At step 635, the processor 701 receives the EOG signal 740 from the EOG sensor 704.

At step 640, the processor 701 determines whether the EOG signal 740 needs calibration. In some embodiments, the processor 701 computes the difference between an eye position estimated based on the EOG signal 740 at the current frame and another eye position calculated based VOG signal at a keyframe that is close to the current frame. If the difference between the eye positions is larger than a threshold value, the processor 701 determines that there is a bias for the EOG signal and the EOG signal 740 needs calibration. If a calibration is needed, at step 645, the processor 701 calibrates the EOG signal 740 by subtracting the bias from the EOG signal 740. At step 650, the processor 701 analyzes the EOG signal to identify a current position of the user's eye. Then the process 600 goes back to step 625 to determine whether the next frame is a regular frame or a keyframe.

The VOG sensor 703 only turns on and operates for a specific amount of time (at the keyframes). For the rest of time, the eye tracking device only uses the EOG sensor 704 for eye tracking. A device performing the process 600 consumes less power than a conventional eye tracking device that keeps a VOG sensor turned on throughout the operation. In addition, the processor 701 only analyzes the VOG signals when the VOG sensor 703 is on. Since it takes less computing time for analyzing the EOG signals from the EOG sensor 704 than analyzing the VOG signals from the VOG sensor 703, the process 600 has an advantage of low latency over a conventional process of keeping a VOG sensor turned on throughout the operation.

In some alternative embodiments, instead of using the processor 701 to track the frame rates of the VOG sensor 703 and the EOG sensor 704, the VOG sensor 703 and the EOG sensor 704 can track their own frame rates. For example, the VOG sensor 703 can track its frame rate and turn it on automatically at each keyframe. Similarly, the EOG sensor 704 can track its own frame rate and operate automatically at each regular frame. Some of the regular frames may overlap with the keyframes at certain points in time.

In some embodiments, the eye tracking device can use other types of low-power sensors instead of EOG sensors. For example, the eye tracking device can use one or more photodiodes (or other type(s) of photosensors) to identify an average intensity of the light reflected by the eye. The average intensity values are enough for the eye tracking device to determine whether the eyes remain still or move. A machine learning model (e.g., a neural network model) can be trained for the determination. In other words, if the average intensity value of an eye changes to a certain extent, the eye tracking device recognizes that the corresponding eye moves.

Alternatively, the eye tracking device can use a low-power camera as a low-power sensor. For example, a 1 mm×1 mm camera sensor (e.g., a complementary metal-oxide-semiconductor (CMOS) sensor or a charge-coupled device (CCD) sensor) with a low resolution can be a low-power sensor and have a level of power consumption that is much lower than the level of power consumption of a typical VOG sensor camera. Also because of the low resolution, the low-power camera needs less time to process the video sequence of the low-power camera and achieves a low latency for eye tracking.

Figure 8:
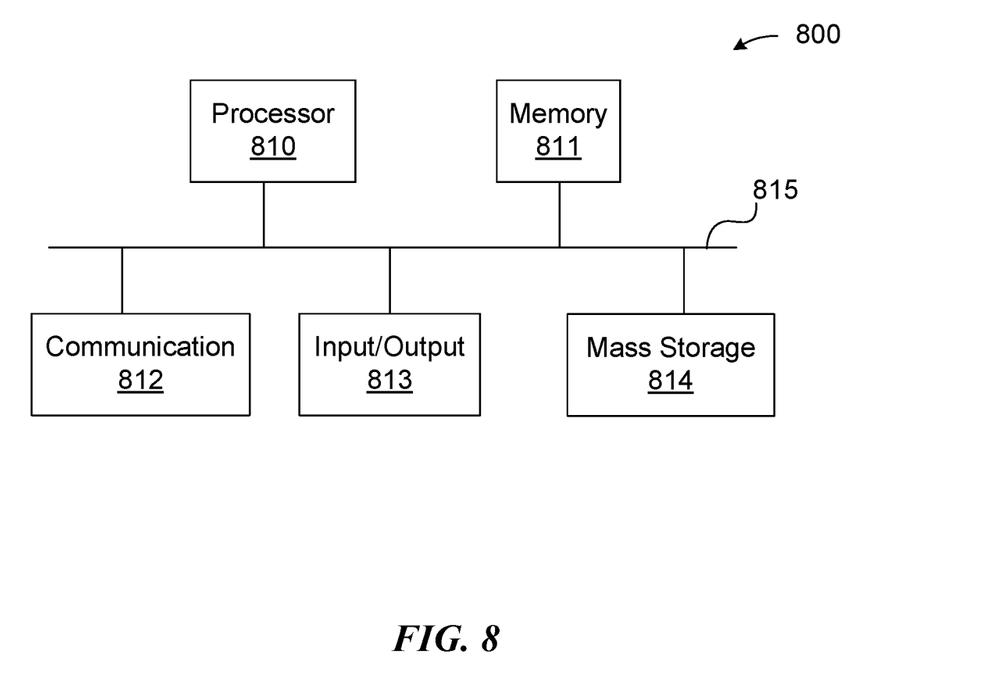
FIG. 8 shows a high-level example of a hardware architecture of a system that can be used to implement any one or more of the functional components described herein.

FIG. 8 shows a high-level example of a hardware architecture of a processing system that can be used to implement the disclosed functions. The processing system illustrated in FIG. 8 can be, e.g., a subsystem of the HMD device or other eye tracking devices. One or multiple instances of an architecture such as shown in FIG. 8 (e.g., multiple computers) can be used to implement the techniques described herein, where multiple such instances can be coupled to each other via one or more networks.

The illustrated processing system 800 includes one or more processors 810, one or more memories 811, one or more communication device(s) 812, one or more input/output (I/O) devices 813, and one or more mass storage devices 814, all coupled to each other through an interconnect 815. The interconnect 815 may be or include one or more conductive traces, buses, point-to-point connections, controllers, adapters and/or other conventional connection devices. Each processor 810 controls, at least in part, the overall operation of the processing device 800 and can be or include, for example, one or more general-purpose programmable microprocessors, digital signal processors (DSPs), mobile application processors, microcontrollers, application specific integrated circuits (ASICs), programmable gate arrays (PGAs), or the like, or a combination of such devices.

Each memory 811 can be or include one or more physical storage devices, which may be in the form of random access memory (RAM), read-only memory (ROM) (which may be erasable and programmable), flash memory, miniature hard disk drive, or other suitable type of storage device, or a combination of such devices. Each mass storage device 814 can be or include one or more hard drives, digital versatile disks (DVDs), flash memories, or the like. Each memory 811 and/or mass storage 814 can store (individually or collectively) data and instructions that configure the processor(s) 810 to execute operations to implement the techniques described above. Each communication device 812 may be or include, for example, an Ethernet adapter, cable modem, Wi-Fi adapter, cellular transceiver, baseband processor, Bluetooth or Bluetooth Low Energy (BLE) transceiver, or the like, or a combination thereof. Depending on the specific nature and purpose of the processing system 800, each I/O device 813 can be or include a device such as a display (which may be a touch screen display), audio speaker, keyboard, mouse or other pointing device, microphone, camera, etc. Note, however, that such I/O devices may be unnecessary if the processing device 800 is embodied solely as a server computer.

In the case of a user device, a communication device 812 can be or include, for example, a cellular telecommunications transceiver (e.g., 3G, LTE/4G, 5G), Wi-Fi transceiver, baseband processor, Bluetooth or BLE transceiver, or the like, or a combination thereof. In the case of a server, a communication device 812 can be or include, for example, any of the aforementioned types of communication devices, a wired Ethernet adapter, cable modem, DSL modem, or the like, or a combination of such devices.

The machine-implemented operations described above can be implemented at least partially by programmable circuitry programmed/configured by software and/or firmware, or entirely by special-purpose circuitry, or by a combination of such forms. Such special-purpose circuitry (if any) can be in the form of, for example, one or more application-specific integrated circuits (ASICs), programmable logic devices (PLDs), field-programmable gate arrays (FPGAs), system-on-a-chip systems (SOCs), etc.

Software or firmware to implement the embodiments introduced here may be stored on a machine-readable storage medium and may be executed by one or more general-purpose or special-purpose programmable microprocessors. A "machine-readable medium," as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Examples of Certain Embodiments

Certain embodiments of the technology introduced herein are summarized in the following numbered examples:

1. A apparatus of eye tracking, including: means for operating a first sensor that has a first level of power consumption to track positions of an eye of a user; means for stopping operation of the first sensor in response to a detection that the eye does not change position for a time period; means for operating a second sensor that has a second level of power consumption to detect a change of position of the eye, the second level of power consumption being lower than the first level of power consumption; and means for resuming operation of the first sensor in response to detection, by the second sensor, of the change of the position of the eye.

2. The apparatus of example 1, wherein the first sensor has a first signal processing latency that is higher than a second signal processing latency of the second sensor.

3. The apparatus of example 1 or 2, wherein the first sensor has a first eye-tracking accuracy that is greater than a second eye-tracking accuracy of the second sensor.

4. The apparatus in any of the preceding examples 1 through 3, wherein the first sensor includes a camera that captures images of the eye of the user.

5. The apparatus in any of the preceding examples 1 through 4, wherein the second sensor includes an electrooculography sensor, a photodiode, or a low-power camera sensor.

6. The apparatus in any of the preceding examples 1 through 5, further including: means for estimating eye positions based on signals of the second sensor at two frames and calculating a difference between the two eye positions; and means for recognizing the change of the position of the eye when the difference between the two eye positions exceeds a threshold.

7. The apparatus in any of the preceding examples 1 through 6, further including: means for continuing operation of the second sensor when the operation of the first sensor resumes.

8. An electronic device for eye tracking, including: a first sensor that has a first level of power consumption, to track positions of an eye of a user; a second sensor that has a second level of power consumption, to track positions of the eye of the user, the second level of power consumption being lower than the first level of power consumption; and a processor configured to execute a process including: detecting that the eye does not change position for a time period based on signals from the first sensor; stopping operation of the first sensor; triggering the second sensor to detect a change of position of the eye; and resuming operation of the first sensor in response to the change of the position of the eye.

9. The electronic device of example 8, further including: a third sensor having the first level of power consumption that tracks positions of another eye of the user, the third sensor and the first sensor being of the same type; and a fourth sensor having the second level of power consumption that tracks positions of the other eye of the user, the fourth sensor and the second sensor being of the same type.

10. The electronic device of example 8 or 9, further including: a light source that generates light that is reflected by the eye and captured by the first sensor or the second sensor.

11. The electronic device in any of the preceding examples 8 through 10, further including: a control circuit that controls the operation of the first sensor based on instructions from the processor.

12. The electronic device in any of the preceding examples 8 through 11, wherein the processor is further configured to: estimate eye positions based on signals of the second sensor at two frames and calculating a difference between the two eye positions; and recognize the change of the position of the eye if the difference between the two eye positions exceeds a threshold.

13. The electronic device in any of the preceding examples 8 through 12, wherein the first sensor has a first signal processing latency that is higher than a second signal processing latency of the second sensor, or the first sensor has a first eye-tracking accuracy that is better than a second eye-tracking accuracy of the second sensor.

14. The electronic device in any of the preceding examples 8 through 13, where the first sensor is a video oculography sensor, and the second sensor is an electrooculography sensor, a photodiode, or a low-power camera sensor.

15. A apparatus of eye tracking, including: means for operating a first sensor that has a first level of power consumption to track positions of an eye of a user at a first frame rate; means for determining positions of the eye at keyframes based on signals collected from the first sensor at the first frame rate; means for operating a second sensor that has a second level of power consumption to track positions of the eye of the user at a second frame rate, the second level of power consumption being lower than the first level of power consumption, the first frame rate being lower than the second frame rate; and means for determining positions of the eye at regular frames based on signals collected from the second sensor at the second frame rate.

16. The apparatus of example 15, further including: means for generating a bias between an eye position determined based on signals collected from the first sensor at a keyframe and another eye position determined based on signals collected from the second sensor at a regular frame; and means for calibrating multiple eye positions determined based on signals from the second sensor by subtracting the bias from the multiple eye positions.

17. The apparatus of example 15 or 16, wherein the first sensor has a first signal processing latency that is higher than a second signal processing latency of the second sensor.

18. The apparatus in any of the preceding examples 15 through 17, wherein the first sensor has a first eye-tracking accuracy that is better than a second eye-tracking accuracy of the second sensor.

19. The apparatus in any of the preceding examples 15 through 18, wherein the second sensor includes an electrooculography sensor, a photodiode, or a low-power camera sensor.

20. The apparatus in any of the preceding examples 15 through 19, further including: means for determining a fixation point at a user interface based on the position of the eye being tracked; and means for conducting a foveated rendering of the user interface based on the fixation point.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and that (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

What is claimed is:

1. A method of eye tracking, comprising:
   operating a video oculography (VOG) sensor to track a position of an eye of a user;
   stopping operation of the VOG sensor in response to a first detection, based on VOG signals from the VOG sensor, that the eye does not change position for a time period;
   operating an electrooculography (EOG) sensor to track the position of the eye responsive to stopping the operation of the VOG sensor, wherein the EOG sensor has a lower power consumption than the VOG sensor; and
   resuming operation of the VOG sensor in response to a second detection, based on EOG signals from the EOG sensor, of a change of the position of the eye.

2. The method of claim 1, wherein the VOG sensor has a first signal processing latency that is higher than a second signal processing latency of the EOG sensor.

3. The method of claim 1, wherein the VOG sensor has a first eye-tracking accuracy that is greater than a second eye-tracking accuracy of the EOG sensor.

4. The method of claim 1, wherein the VOG sensor comprises a camera that captures images of the eye of the user.

5. The method of claim 1, wherein the EOG sensor comprises a low-power camera.

6. The method of claim 1, further comprising:
   estimating two eye positions based on the EOG signals of the EOG sensor at two frames and calculating a difference between the two eye positions; and
   recognizing the change of the position of the eye when the difference between the two eye positions exceeds a threshold.

7. The method of claim 1, further comprising:
   continuing operation of the EOG sensor when the operation of the EOG sensor resumes.

8. An electronic device for eye tracking, comprising:
   a viedo oculography (VOG) sensor to track a position of an eye of a user;
   an electrooculography (EOG) sensor to track the position of the eye of the user, wherein the EOG sensor has a lower power consumption than the VOG sensor; and
   a processor configured to execute a process including:
      detecting, based on VOG signals from the VOG sensor, that the eye does not change position for a time period;
      stopping operation of the VOG senror in response to detecting that the eye does not change position for the time period;
      triggering the EOG sensor to track the position of the eye responsive to stopping the operation of the VOG sensor; and
      resuming operation of the VOG sensor in response to a detection, based on EOG signals of the EOG sensor, of a change of the position of the eye.

9. The electronic device of claim 8, further comprising:
   another VOG sensor that tracks positions of another eye of the user; and
   another EOG sensor that tracks the positions of the another eye of the user.

10. The electronic device of claim 8, further comprising:
    a light source that generates light that is reflected by the eye and captured by the VOG sensor or the EOG sensor.

11. The electronic device of claim 8, further comprising:
    a control circuit that controls an operation of the VOG sensor based on instructions from the processor.

12. The electronic device of claim 8, wherein the processor is further configured to:
    estimate two eye positions based on the EOG signals of the EOG sensor at two frames;
    calculate a difference between the two eye positions; and
    recognize the change of the position of the eye when the difference between the two eye positions exceeds a threshold.

13. The electronic device of claim 8, wherein the VOG sensor has a first signal processing latency that is higher than a second signal processing latency of the EOG sensor, or the VOG sensor has a first eye-tracking accuracy that is better than a second eye-tracking accuracy of the EOG sensor.

14. The electronic device of claim 8, where the VOG sensor is a camera, and the EOG sensor comprises a low-power camera.

15. A method of eye tracking, comprising:
    operating a video oculography (VOG) sensor to track positions of an eye of a user at a first frame rate;
    determining the positions of the eye at keyframes based on VOG signals collected from the VOG sensor at the first frame rate, wherein the VOG sensor stops operating based on the eye remaining in a fixed position for a time period;
    operating am electrooculography (EOG) sensor to track the positions of the eye of the user at a second frame rate upon stopping an operation of the VOG sensor, wherein the EOG sensor has a lower power consumption than the VOG sensor, wherein the first frame rate is lower than the second frame rate;
    determining the positions of the eye at regular frames based on EOG signals collected from the EOG sensor at the second frame rate;
    determining a fixation point at a user interface based on a current position from the fixed position of the eye being tracked;
    conducting a foveated rendering of the user interface based on the fixation point; and
    resuming operation of the VOG sensor in response to a detection, based on the EOG signals from the EOG sensor, of a change of a position of the eye.

16. The method of claim 15, further comprising:
    generating a bias between an eye position determined based on the VOG signals collected from the VOG sensor at a keyframe and another eye position determined based on the EOG signals collected from the EOG sensor at a regular frame; and calibrating multiple eye positions determined based on the EOG signals from the EOG sensor by subtracting the bias from the multiple eye positions.

17. The method of claim 15, wherein the VOG sensor has a first signal processing latency that is higher than a second signal processing latency of the EOG sensor.

18. The method of claim 15, wherein the VOG sensor has a first eye-tracking accuracy that is better than a second eye-tracking accuracy of the EOG sensor.

19. The method of claim 15, wherein the EOG sensor comprises a low-power camera sensor.

* * * * *